(12) United States Patent
McClure et al.

(10) Patent No.: US 6,275,734 B1
(45) Date of Patent: Aug. 14, 2001

(54) EFFICIENT GENERATION OF SENSING SIGNALS IN AN IMPLANTABLE MEDICAL DEVICE SUCH AS A PACEMAKER OR ICD

(75) Inventors: Kelly H. McClure, Simi Valley; Gabriel Mouchawar, Newhall, both of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/223,422

(22) Filed: Dec. 30, 1998

(51) Int. Cl.$^7$ ....................................................... A61N 1/37
(52) U.S. Cl. .................................................................. 607/27
(58) Field of Search .................................................. 607/27

(56) References Cited

U.S. PATENT DOCUMENTS 5,685,315   11/1997   McClure et al. ..................... 128/708

Primary Examiner—William E. Kamm

(57) ABSTRACT

An implantable cardiac device such as a pacemaker or an implantable cardioverter defibrillator (ICD) that stores a broad band electrogram signal in response to the detecting of a particular cardiac event. The system includes an external programmer which is capable of accessing the stored electrogram via a telemetry circuit so that the stored electrogram can be downloaded and reviewed on a display of the external programmer. The external programmer is also equipped with a digital filter emulator that is capable of emulating the filtering of the broad band electrogram signal that is being provided to the processor of the implanted cardiac device. The emulator therefore allows a treating physician to review an emulation of the waveform that the processor of the implanted cardiac device is seeing when the processor is initiating the delivery of therapeutic electrical stimulation to the heart.

12 Claims, 3 Drawing Sheets

EFFICIENT GENERATION OF SENSING SIGNALS IN AN IMPLANTABLE MEDICAL DEVICE SUCH AS A PACEMAKER OR ICD

FIELD OF THE INVENTION

The present invention relates to an implantable medical device for monitoring and possibly providing therapeutic electrical stimulation to a patient's organ and, more particularly, concerns an implantable medical device, such as a pacemaker or implantable cardioverter defibrillator, that receives a sense signal indicative of the function of the organ and filters this signal, and is further capable of providing portions of the sense signal to an external monitoring device via a telemetry circuit.

BACKGROUND OF THE INVENTION

Implantable medical devices, such as implantable cardiac devices, are devices which are implanted in the body of a patient and are capable of monitoring the function of a patient's organ, such as their heart or brain, and are further configured in some instances to be able to deliver therapeutic electrical stimulation to the patient's organ.

Implantable cardiac devices, such as pacemakers and implantable cardioverter defibrillators (ICDs), are very commonly used implantable mechanical devices and are used to treat various heart conditions. These types of implantable cardiac devices typically have one or more leads that are positioned adjacent the walls of the heart and a control unit which receives signals indicative of the functioning of the heart. The control unit induces the delivery of therapeutic electrical stimulation to the walls of the heart via the leads in response to sensed heart conditions. Generally, the control unit incorporates a processor that is capable of recognizing and discerning particular heart irregularities based upon the signals that the processor receives. The implanted leads act as a sensor which delivers an intracardial electrogram (IEGM) to the processor, which provides the processor with a signal that is indicative of the heart function. Hence, the processors of these types of implantable cardiac devices continuously receive an IEGM signal that allows the processor to determine whether therapeutic stimulation of the heart is needed to regulate the heart function.

Generally, the IEGM signal that is provided by the lead is initially sampled by the sensor at a fairly wide bandwidth which results in a broad spectrum signal indicative of the function of the heart. However, this cardiac rate sensing IEGM signal is typically filtered so that the processor receives a narrower bandwidth signal which can be used by the processor to detect thresholds for delivering therapeutic electrical stimulation. In one application, the narrow band signal provides the processor with a signal that is indicative of the R wave and the T wave is filtered out of the signal so that the processor can get an accurate determination of the intrinsic heart rate of the patient.

Typically, the bandwidth of the IEGM signal that is used by the processor as a heart rate sensor input, is selected to be narrower than the bandwidth of the original IEGM signal. For example, in current generation pacemakers manufactured by PACESETTER, INC. of Sylmar, Calif., the bandwidth of the IEGM signal provided by the implanted leads can be between 1 and 100 Hz. However, the filtered electrogram that is provided to the processor on a sense channel input is on the order of 10 to 60 Hz for an ICD 20 to 120 Hz in the pacemaker. The narrower bandwidth signal results in the processor receiving a signal where more components of interest, such as R waves, are more clearly defined, thereby allowing these more clearly defined events to serve as the markers or thresholds for initiating or altering the delivery of pacing, cardioversion or defibrillation therapy.

Hence, these types of implantable cardiac devices essentially develop two or more IEGM signals: a broadband signal from the sensing electrode and narrow band signals that are used by the processor as sense inputs. One problem that arises as the result of the implantable cardiac device effectively generating two or more IEGM signals is that the physicians who are implanting the devices and who are also subsequently reviewing the operation of the device may alternatively desire to see either the regular broad band IEGM signal or the narrow band IEGM signal provided to the processor on the sense channel.

Specifically, most implanted cardiac devices that are used today are capable of storing IEGM signals so that these signals can be subsequently transmitted to a physician for the physician to review on an external programmer. Typically, the external programmer communicates with the implanted device via an RF communications link. When a particular heart episode that necessitates the delivery of corrective stimulation by the implanted cardiac device occurs, the device also initiates a recording process whereby an IEGM signal is recorded in memory for subsequent evaluation. Stored IEGM signals can be transmitted from the memory of the implanted device to the external programmer and then displayed to the physician on a display that is associated with the external programmer. This information can be used by the treating physician to ascertain whether the device is correcting heart function appropriately and can also be used as a diagnostic tool for assessing the progression of the patient's heart disease and for setting sensing detection parameters.

In another application, the treating physician may view the IEGM signal, either at implantation or during a follow up visit, in real time. In these applications, some physicians may want to view the broad band IEGM signal and other physicians may only want to see the narrow band signal that is being provided to the processor. For example, the physician may want to assess the performance of the sensor in obtaining the IEGM signal using the broad band sensor input signal. Alternatively, some physicians may want to view the narrow band signal being provided to the processor to ensure that the filtering of the broad band signal results in an appropriate signal being provided to the processor.

Hence, some physicians will want to see the full bandwidth electrogram signal so as to get a better picture of the heart's function. Other physicians may simply want to look at the narrow band electrogram signal that is being provided to the implanted device on the sense channel so that the physician can review the electrogram signal that is indicative of the cardiac intrinsic rate or device function.

As a result of the competing desires of physicians, many implantable cardiac devices have incorporated multiplexers that receive both the broad band electrogram signal from the leads and also the filtered narrow band sense electrogram signal. These systems typically store only the signal that is selected by the treating physician as the signal to be stored. Subsequently, when a physician wishes to review the electrogram signal, the signal is then provided via the telemetry circuit to the external programmer. Hence, in the typical prior art, implanted cardiac devices must incorporate additional circuitry and control lines so as to be able to store in the memory either the broad band electrogram signal or the narrow band sense electrogram signal. This additional circuitry and control lines occupies limited space within the control unit of the cardiac device and further consumes limited power that is provided by the battery, thereby shortening the life of the implanted cardiac device. If the narrow and broad band signals are stores, the storage time is reduced by half.

Moreover, with most implanted cardiac devices, once the treating physician has selected which of the electrogram signals they wish to have stored, the other electrogram signal cannot be seen by the treating physician as it was not stored in the memory of the implanted cardiac device. This lack of flexibility is, of course, compounded by the fact that the physician who makes the initial selection as to which electrogram is to be stored may not be the same physician who will be subsequently reviewing the stored electrogram for follow up treatment of the patient and to follow-up on the performance of the implanted cardiac device.

Hence, there is a need for an implantable cardiac system which is capable of allowing a treating physician to subsequently view recorded electrograms of heart events having different bandwidths via an external programmer without requiring additional components and circuitry to be implanted in the body of the patient. To this end, there is a need for an external programmer that is adapted to provide the physician with either the wide band electrogram or the narrow band sense channel electrogram signal.

SUMMARY OF THE INVENTION

The aforementioned needs are satisfied by the implantable system of the present invention which is comprised of an implantable device having a sensor that is adapted to be implanted within the body of a patient adjacent an organ of the patient so as to be able to sense activity of the organ. There may be more than one narrow band filter, each designed to accentuate a certain part of the signal. The implantable device also includes a processor and a memory. The processor receives a broad bandwidth signal from the sensor and selectively stores this broad bandwidth signal in the memory. The device also includes a filter that filters the broad bandwidth signal into a narrow bandwidth signal and provides the narrow bandwidth signal to the processor so that the processor can use the narrow bandwidth signal to assess the intrinsic activity of the organ. The implantable device is also adapted to be communicatively linked to an external programmer so as to be able to provide the stored broad band signal to the external programmer. The external programmer includes an emulator that is adapted to digitally process the stored broad band signal so as to produce an emulated narrow band signal that corresponds to the narrow band sense signal that is provided to the processor of the implanted device.

In one aspect, the present invention comprises an implantable cardiac device system which includes an implantable cardiac device that includes a sensor adapted to be positioned adjacent a wall of the heart, a processor, and a memory, wherein the processor receives a broad bandwidth electrogram signal from the sensor and selectively stores this broad bandwidth signal in the memory and wherein the implanted cardiac device further includes a sense channel that processes the broad bandwidth electrogram signal so that the processor receives a narrow band sense electrogram signal. The implantable cardiac device is also adapted to be communicatively linked to an external programmer so as to be able to provide the stored broad band electrogram signal to the external programmer wherein the external programmer includes an emulator that is adapted to digitally process the stored broad band electrogram signal so as to produce an emulated sense electrogram signal that corresponds to the sense electrogram provided to the processor of the implanted cardiac device.

Hence, in one aspect the invention is comprised of an implantable cardiac device system that is sensing a broad band electrogram signal via a lead that is implanted within the heart of the patient and is receiving a filtered electrogram signal via a sense channel. Upon the occurrence of a particular cardiac event, the implantable cardiac device stores a signal representative of the broad band signal. The system further includes an external programmer that is adapted to receive the stored broad band signal and then digitally filter the IEGM signal to emulate the sense channel input that is being provided to the processor of the implanted cardiac device.

In one embodiment, the external programmer of the implantable system is adapted to allow the treating physician to view both the broad bandwidth signal and an emulated narrow bandwidth signal in real time it will be appreciated that the treating physician may want to be able to view either or both of these signals in real time to assess the performance of the patient's organ or to assess the performance of the sensing filters that are providing the narrow band signal. In some applications, the sensing filters will comprise digital filters that can be configured by the treating physician via the external programmer. Hence, the ability to review an emulated narrow band signal allows the physician to adjust the performance of the sense channel filters so that the processor can receive a sense channel input that is better configured for the patient's condition.

The implantable cardiac device system of the present invention thereby eliminates the need for additional circuitry and components to be positioned within the implantable cardiac device casing to store or transmit either the broad band or narrow band electrogram for subsequent transmission to the external programmer via a telemetry circuit. Moreover, the physician who is reviewing the downloaded signal on the external programmer can select between the broad band signal or the emulation of the narrow band sense channel signal as needed. Further, the external programmer can be adapted to have a plurality of digital filters each of which is selected to emulate the various types of sense channel amplifiers and filters that are positioned within a variety of implanted cardiac devices. This can also be used to select and configure filters.

These and other objects and advantages of the present invention will become more fully apparent from the following description taken in conjunction with the accompanying drawings.

DETAILED DESCRIPTION OF THE INVENTION

Figure 1:
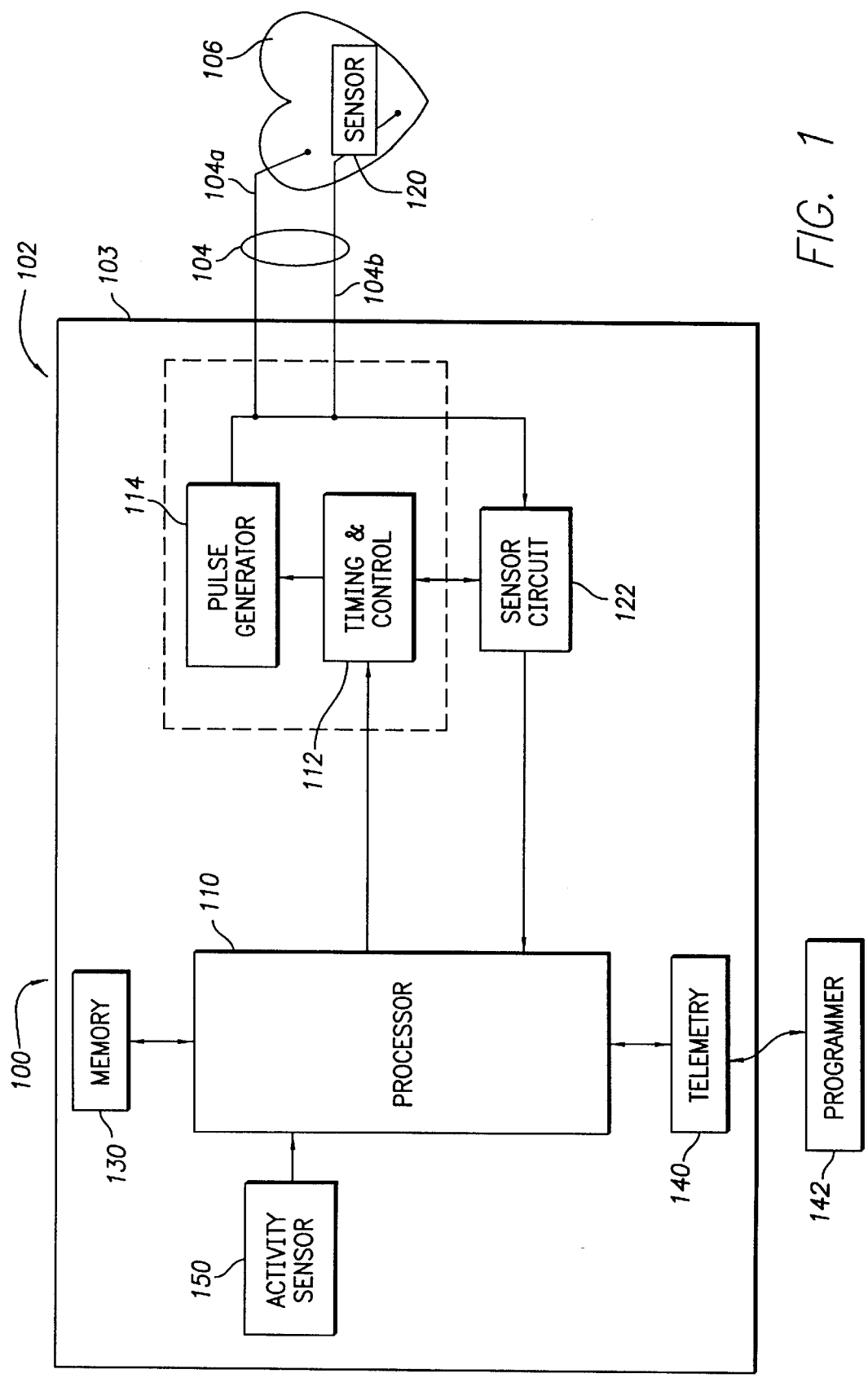
FIG. 1 is a functional block diagram of one embodiment of an implantable cardiac device.

Reference will now be made to the drawings wherein like numerals refer to like parts throughout. Referring to FIG. 1, a functional block diagram of one embodiment of an implantable medical device system 100 is shown, which is generally positioned within a casing 103 that is adapted to be implanted in the body of a patient in a well-known manner, and a plurality of leads 104a and 104b that are adapted to be positioned within the chambers of a patient's heart 106. The implantable cardiac device 100 can be comprised of any implantable device including a pacemaker or an implantable cardioverter defibrillator (ICD) or any implantable device incorporating the functionality of both a pacemaker and an ICD. While the preferred embodiment discusses the present invention in connection with an implantable cardiac device, it will be appreciated from the following discussion that the present invention can be used in conjunction with any implantable device that includes a sensor which measures the intrinsic activity of one of the patient's organs and provides a filtered narrow band signal to the processor of the implanted device. Other devices may include neural devices for providing therapeutic stimulation to portions of the brain and devices that monitor organ activity such as ECG monitors, brain-wave monitors and other types of monitors known in the art.

In this embodiment, the control unit 102 includes a processor 110 which provides output signals to a timing and control circuit 112. Upon receipt of the output signals from the processor 110, the timing and control circuit 112 induces a pulse generator 114 to produce therapeutic electrical stimulation, e.g., pacing pulses or cardioversion or defibrillation waveforms, that is transported via the leads 104 to thereby stimulate the heart 106. The exact function of the processor 110 in inducing the delivery of the therapeutic electrical stimulation to the heart is performed in any of a number of well-known manners. In one embodiment, the processor 110 induces pacing pulses to be delivered to the apex of the ventricle of the heart 106. In another embodiment, the processor 110, upon sensing the occurrence of a particular tachycardia, induces defibrillation or cardioversion stimuli to be delivered to the heart between one or more of the leads 104 and the casing 103.

Further, the processor 110 receives input signals from a sensor 120 via a sensor circuit 122. In one embodiment, the sensor 120 is actually comprised of an implanted lead 104 that is positioned within one of the chambers of the heart 106 so as to provide an intracardiac electrogram (IEGM) signal to the processor 110. The IEGM signal is generally a wide band signal having a bandwidth of 1 to 100 Hz. The wide band IEGM signal is provided to the sensor circuit 122 and is further processed by the sensor circuit 122 so that the processor 110 receives a filtered IEGM signal that the processor 110 can use in determining whether to deliver therapeutic electrical stimulation to the heart via the timing and control circuit 112 and the pulse generator circuit 114.

The processor 110 also has an associated memory 130 wherein information, such as IEGM signals, can be stored for subsequent downloading to an external programmer 142 via a telemetry circuit 140. As will be discussed in greater detail below, the process by which IEGM signals can be stored in the memory 130 by the processor 110, in this embodiment, is simplified versus the process by which this same task is performed in prior art implanted devices thereby simplifying the implanted cardiac device 100 and also reducing the consumption of power by the components of the implanted cardiac device 100.

The processor 110 may also receive signals from an activity sensor 150 which allows the processor 110 to modify the delivery of therapeutic electrical stimulation to the heart 106. The implantable cardiac device 100 provides therapy to the heart 106 in a manner that is substantially identical to the manner of prior art implantable cardiac devices. Specifically, in one embodiment, the implanted cardiac device 100 is adapted to be a pacemaker, in another embodiment, the implanted cardiac device is adapted to be a cardioverter defibrillator, and in yet a third embodiment, the implanted cardiac device is adapted to have both the functionality of a pacemaker or an ICD. As discussed above, the present invention should not be limited to implanted cardiac devices. Rather, the principles of the present invention can be used in other implanted devices including cardiac monitoring devices, neural monitoring and stimulating devices and other implanted devices for monitoring or stimulating various patient organs.

Figure 2:
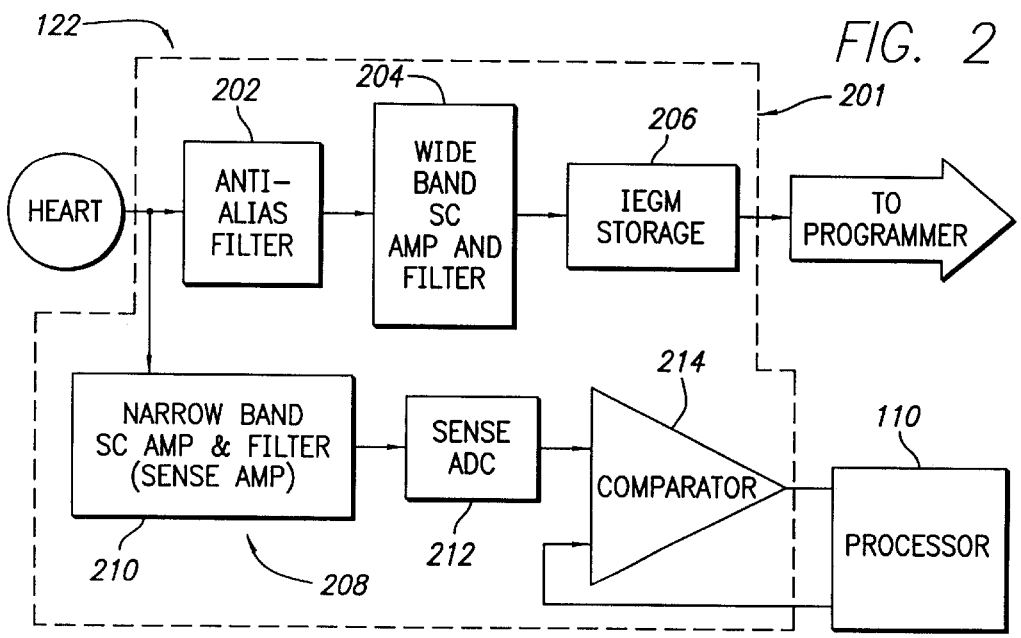
FIG. 2 is a functional block diagram of one embodiment of a system for obtaining a signal indicative of the function of an organ and for filtering the signal so as to provide a processor of the implantable device of FIG. 1 with a narrower bandwidth signal.

FIG. 2 is a block diagram which illustrates one embodiment of the sensor circuit 122 that receives a broad band IEGM signal from the sensor 120 that is implanted within the heart 106. As is understood in the art, the sensor 120 is comprised of one or more of the leads 104 that are implanted within the chambers of the heart so as to be able to provide an intracardiac electrogram (IEGM) signal in a well known manner. This signal is indicative of the functioning of the heart and the signal provided by the sensor 120 can be used by the processor 110 to ascertain whether certain criteria have been met that necessitate the delivery of therapeutic electrical stimulation to the heart to regulate heart function.

For example, the processor 110 may review the IEGM signal and, upon detecting a ventricular tachycardia or fibrillation, may induce a cardioversion or defibrillation shock to be delivered by the leads 104 in a manner that is known in the art. Similarly, the processor 110 may also use the IEGM signal as a basis for delivering a pacing pulse to the apex of the ventricle of the heart 106 so as to induce a paced heart activity in a demand pacing regime.

As discussed above, the IEGM signal from the implanted sensor 120 is initially provided to the sensor circuit 122. The processor 110 is adapted to store the broad band IEGM signal upon the occurrence of a particular event. As is understood in the art, the IEGM signal that occurs during a particular heart activity is often stored in the memory 130 so that the signal can be subsequently downloaded, via the telemetry circuit 140 to the external programmer 142, to allow a treating physician to subsequently observe the recorded cardiac event and ensure that the implanted cardiac device 100 applied the appropriate therapy for the particular patient.

Typically, in the prior art, the physician implanting the device would initially configure the control unit 102 of the device so that either a broad band IEGM signal or a narrow band sense signal would be stored in the memory 130 for subsequent downloading to the treating physician. As discussed above, it is often desirable for treating physicians to be able to see the entire broad band electrogram signal and, in other applications, it is more desirable to see the narrow band sense electrogram signal that is being received by the processor 110.

In particular, the processor 110 of an implanted cardiac device typically receives a narrow band electrogram signal that is filtered so that only particular characteristics of the electrogram signal are provided to the processor 110. This allows the processor 110 to simply determine whether a particular cardiac event has occurred so as to allow the processor 110 to initiate the appropriate therapeutic response. Treating physicians would like to see the sense channel electrogram signal that is being received by the processor 110 to verify that the processor 110 is functioning correctly.

Consequently, implanted cardiac devices of the prior art are adapted to store either the broad band electrogram signal or the narrow band sense channel electrogram signal that is being received by the processor 110 corresponding to a particular cardiac event. However, as discussed above, the selection between the two stored signals is made at the time of implantation or during a follow-up visit to the doctor which limits the information that can subsequently be telemetered to the external programmer 142 for review. Further, the storage of either the sense electrogram signal or the broad band electrogram signal typically requires additional components to be used within the implanted device. In particular, this storage technique typically requires an additional multiplexer which consumes space and power from the battery of the implanted device. Moreover, if both the broad band signal and the narrow band signal are stored in the memory, the duration of signals that can be stored is significantly reduced.

Referring now to FIG. 2, the sensor circuit 122 of the preferred embodiment will now be described in greater detail. Specifically, the implanted sensors 120 (See, FIG. 1) and 104 sense a broad band electrogram signal to the sensor circuit 122 which is provided to both a broad band storage channel 201 and a narrow band sense channel 208. The narrow band sense channel 208, in this particular implementation, initially includes a filter/amplifier 210 which receives the broad band IEGM signal from the sensors 120 and 104 that is positioned within the heart 106 and filters this signal so as to highlight the characteristic waveforms which the processor 110 will use to ascertain whether the heart 106 is in need of a therapeutic electrical stimulation. In this implementation, the filter 210 is described as being a switched capacitor filter/amplifier, however, it will be appreciated that any of a number of different filtering devices, including digital filters that provide an output which is a function of the current input and previous inputs or outputs, can be used without departing from the spirit of the present invention.

In one embodiment, the sensors 120 and 104 are providing a broad band signal in the range of between approximately 0.1 to 400 Hz. The narrow band filter 210 preferably filters the signal so that only signals in the 1.0 to 100 Hz range are detected. It will be appreciated that an R wave corresponding to ventricular depolarization generally has most of its energy in the 20 to 90 Hz range so that the filter 210 can then filter the incoming broad band signal so that the R wave can be edge detected to thereby allow for the processor 110 to apply or withhold therapeutic electrical stimulation as necessary. It will be appreciated that the sensor circuit 122 can be adapted to provide similar filtering for any physiological input, such as atrial waves from a sensor implanted within the atrium of the heart or other physiological circuits, without departing from the spirit of the present invention.

The signal from the filter 210 on the sense channel is then provided to an analog to digital converter (ADC) 212. The ADC 212 converts the analog signal to a digital signal and then provides a digital output signal to a digital window comparator 214. The comparator 214 compares the incoming digital signal from the sense ADC 212 to one or more preset values that are provided by the processor 110 in a manner similar to that described in Assignee's U.S. Pat. No. 5,685,315. The preset values are preferably selected so that when the value being provided by the ADC is over the preset value, the comparator 214 sends a signal to the processor 110 indicating that a particular event, e.g., an R wave corresponding to ventricular depolarization, or a P wave corresponding to atrial depolarization, has occurred. In this way, the processor 110 can use the IEGM signal as a basis for providing or withholding therapeutic electrical stimulation with the risk of the processor 110 triggering incorrect therapeutic stimulation being reduced as a result of the processor 110 only sampling signals within a particular narrow frequency range that is selected to be indicative of particular heart activities such as a ventricular or atrial depolarization.

As is also shown in FIG. 2, the broad band IEGM signal is also provided to a broad band storage channel 201 wherein the signal will be stored in its entirety by the processor 110. Specifically, the broad band IEGM signal from the sensors 120 and 104 are initially provided to an anti-alias filter 202 and it is then provided to a wide band amp and filter 204. The processor 110 is adapted to record the sampled broad band IEGM signal from the filter 204 in the memory 130 upon determining from the sense channel input 208 that the heart 106 is experiencing abnormal heart activity. Preferably, the processor 110 records a predetermined portion of the broad band IEGM signal and the resulting therapy so that a record is developed in the memory 130 that is indicative of the heart event and the resulting therapy that was applied by the implanted cardiac device 100. This record can then be subsequently downloaded to the external programmer 142 (FIG. 1) to allow a treating physician to review the record to review the heart function and the device function during the episode.

Specifically, the stored signal can be subsequently downloaded to the external programmer 142 via the telemetry circuit 140 in the manner that is well-known in the art. The actual storage process of the broad band IEGM signal is implemented by the processor 110 upon sensing the occurrence of a particular cardiac event. The processor 110 then initiates a recording process whereby the processor 110 records the broad band IEGM signal that corresponds to either a preselected number of heartbeats or records the signal for a preselected period of time. In this way, a record of the heart activity of the patient during particular cardiac events can be stored for subsequent review and analysis by a treating physician. Hence, the sensor circuit 122 of the preferred embodiment only stores the broad band IEGM signal.

However, as discussed above, it is often desirable that the treating physician be able to review the narrow band sense channel signal that was received and used by the processor 110 to determine whether therapeutic electrical stimulation needed to be applied to the heart 106 to correct heart function. In this way, the treating physician can ascertain whether, for example, the threshold values for the implanted cardiac device 100 are set correctly and can adjust these values, if necessary, by using the external programmer 142 in a well known manner. In this embodiment, the sense channel signal is not stored in the memory 130, however, as will be described in greater detail below in reference to FIG. 3, the external programmer 142 is specifically adapted to use the stored broad band IEGM signal that is stored by the processor 110 in function block 206 (FIG. 2) to emulate the sense channel input signal.

Figure 3:
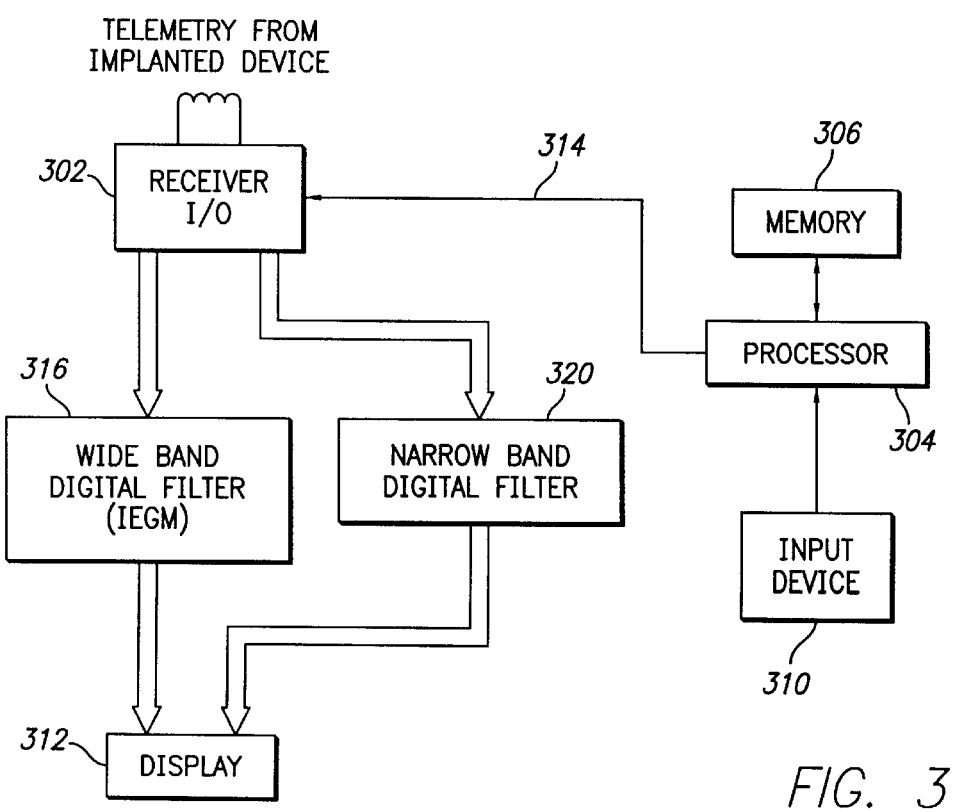
FIG. 3 is a functional block diagram of an external programmer that is adapted to receive a wide band electrogram signal and, upon user selection, is capable of emulating the corresponding narrow band sense channel signal that was provided to the processor of the implanted cardiac device.

Specifically referring to FIG. 3, the external programmer 142 includes a telemetry receiver 302 that is adapted to receive the telemetry signals that are provided to the external programmer 142 (FIG. 1) via the implantable device telemetry circuit 140 (FIG. 1) in a manner that is known in the art. The external programmer 142 also includes a processor 304 which provides signals to the telemetry receiver 302 so as to control the flow of data signals from the receiver 302. The processor 304 also has an associated memory 306 where instructions and telemetered data can be stored by the processor 304 in a well-known manner. The external programmer 142 also includes an input device 310, such as a keyboard, where a treating physician or other user can provide instructions to the processor 304 to induce the external programmer 142 to perform a variety of functions in a manner that is known in the art. The external programmer 142 also includes a display 312 that can display information, such as electrograms and device performance data, to the treating physician.

The external programmer 142 is similar to external programmers of the prior art in that the external programmer 142 allows the treating medical professional to review information that is downloaded from the implanted cardiac device 100 and it further allows the medical professional to send information to the processor 110 of the implanted cardiac device 100 in a manner that is known in the art. Hence, the external programmer 142 allows the medical professional to adjust the operating parameters of the implantable cardiac device 100 based upon the information that is being provided about the operation of the implantable cardiac device 100 to the external programmer 142 via the telemetry circuit 140.

The exemplary block diagram in FIG. 3 has been simplified so as to generally show the components that relate to the display of electrogram data that is either stored in the memory 130 of the implantable cardiac device 100 in the manner that was described above or is being provided to the external programmer 142 in real time. Specifically, the processor 304, in response to a user input via the input device 310, can send a signal to the receiver 302 via a control line 314 so as to induce the receiver 302 to send the telemetered broad band data received from the implanted cardiac device 100 to either a wide band digital filter 316 or a narrow band digital filter 320. The wide band digital filter 316 simply receives the telemetered information and then filters it so that it can be displayed on the display 312 in a manner that is known in the art. This allows the treating physician to view the broad band IEGM signal that was provided by the sensor 120.

Alternatively, the processor 304 can induce the receiver 302 to send the data from the implantable device 100 to a narrow band digital filter 320. The narrow band digital filter 320 in the preferred embodiment is preferably a variable filter which receives the broad band electrogram data that has either been stored in the memory 130 of the implanted cardiac device 100 or is being provided in real time and then digitally filters the broad band signal. The resulting filtered signal from the narrow band digital filter 320 emulates the sense channel signal that is received by the processor 110 via the sense channel 208 of the sensor circuit 120 (FIG. 2) at the time the processor 110 was storing the corresponding broad band signal. In one embodiment, the external programmer 142 is adapted to be able to simultaneously display both the broad band signal and the filtered narrow band signal simultaneously on the display 312.

Specifically, in one exemplary embodiment, the narrow band digital filter 320 and the external programmer 142 are comprised of an infinite impulse response (IIR) filter that has a preselected number of adjustable coefficients $a_j$ and $b_i$ that are selected so as to emulate the actual sense amplifier that is positioned within the implantable cardiac device 100. In this embodiment, the infinite impulse response filter 320 is defined by the following formula:

$$y(n)=\Sigma_{i=0}^{M}b_i x(n-i) -\Sigma_{j=1}^{N}a_j y(n-j)$$

where M=3, N=5, $a_1$=−2.7704, $a_2$=2.9021, $a_3$=−1.4141, $a_4$=0.3097, $a_5$=−0.0201 and $b_0$=0.036, $b_1$=0.1938, $b_2$=−0.5039, $b_3$=0.2742

Hence, the narrow band digital filter 320 is capable of emulating the narrow band filter 210 (FIG. 2) of the implanted cardiac device 100. In one embodiment, the implanted device 100 may include a filter 210 (FIG. 2) that filters the incoming broad band signal from the sensor 120 using this formula. In that embodiment, the emulator in the external programmer is substantially the same as the filter in the implanted device. Emulation may also be accomplished using a finite impulse response filter.

Consequently, the external programmer 142 is capable of taking the broad band IEGM data of a particular cardiac event that was either stored in the memory 130 by the processor 110 or is being provided in real time by the processor 110 and is processing the data so that an emulated sense IEGM waveform can be displayed on the display 312 to the treating physician. In this way, the treating physician can review a signal corresponding to the signal used by the processor 110 to determine how to configure the implantable device 100. Moreover, the implantable cardiac device 100 does not need to include additional lines for multiplexers or memory and the like so as to be able to store one of two separate waveforms.

Further, the external programmer 142 can have a plurality of values stored in memory 306 so that the external programmer 142 can be used to emulate one of a plurality of sense amplifiers 210 (FIG. 2) that are positioned within different implantable cardiac devices 100. It will be appreciated that different sense amplifiers 210 can be used with different implanted devices and that the values can change over time. Hence, the external programmer 142 can be used with a plurality of different implanted sense amplifiers by changing the coefficients $a_j$ and $b_i$ that are used in the infinite impulse response digital filter 320 so that the response corresponds to the analog filter 210 that is actually used in the implanted cardiac device 100. M and N can also be chosen for best emulation.

Figure 4A:
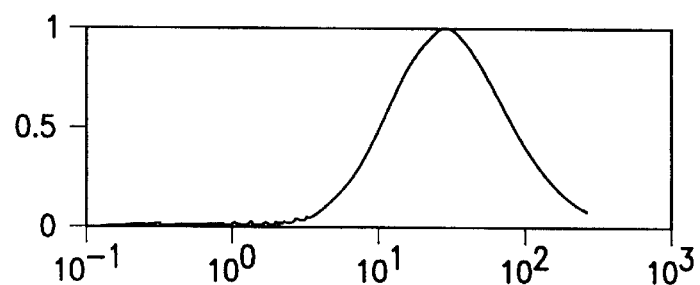
FIG. 4 shows are exemplary plots of both the amplifier amplitude gain (A) and phase (B) versus frequency of the response of a typical ICD sense amplifier as compared to a digital filter approximation of the same.
Figure 4B:
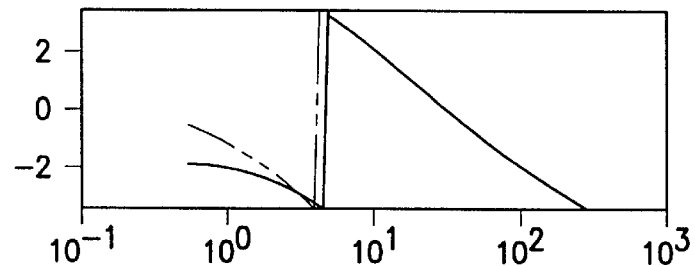

FIG. 4, waveforms A and B are waveforms which illustrate that the digital filter 320 using formula (1) is capable of reproducing the output of the sense amplifier 210 with a high degree of accuracy. Specifically, the top waveform, waveform A, is the amplitude versus the frequency response of an ICD sense analog amplifier 210, which is shown in a solid line, and the corresponding digital filter approximation, shown in a dashed line, using a digital filter 320 as defined by the formula (1) above. By comparing the amplitude values, it will be apparent that there is a high degree of correspondence between the amplitude values of the digital filter approximation and the actual analog amplitude output of the amplifier 210 such that the dashed line of the digital filter actually overlies the solid line of the analog sense amplifier signal.

Similarly, the solid line in the bottom waveform, waveform B, of FIG. 4 is a plot of the phase versus the frequency response of the ICD sense analog amplifier 210, shown in a solid line, and the corresponding digital filter approximation of the same using the formula (1) shown in a dashed line. It can be observed from these waveforms that, with the exception of a phase error at very low frequencies, the digital filter 320 as defined by formula (1) provides a good approximation of the analog ICD sense amplifier filter 210.

Figure 5A:
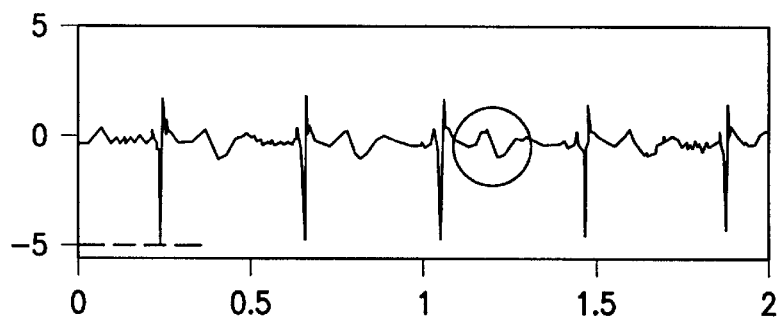
FIG. 5 illustrates an exemplary wide band electrogram of a particular patient and the same signal after being digitally filtered to reflect a sense amplifier bandwidth.
Figure 5B:
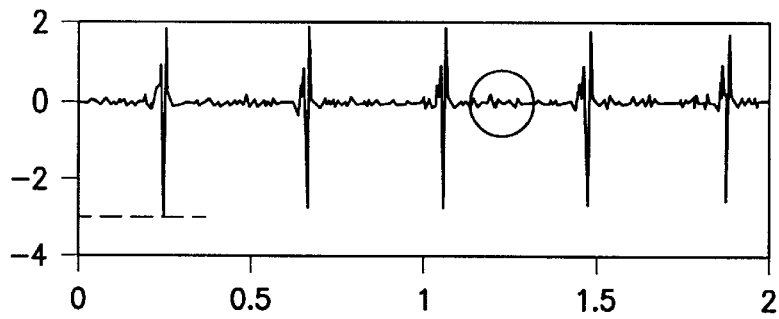

FIG. 5 illustrates the correspondence between the output of the narrow band digital filter 320 of the external programmer 142 as compared to the broad band electrogram signal that is received from the sensor 120. Specifically, the top waveform, waveform A, represents a wide band electrogram sampled at 512 Hz with the particular electrogram segment being from Patient record A175 in the Ann Arbor electrogram database. The electrogram was recorded between the tip and the ring of an implanted catheter. The lower waveform, waveform B, in FIG. 5 is the same electrogram segment after it has been digitally filtered according to the digital filter of formula (1).

In the preferred embodiment, the digital filtering of the narrow band digital filter 320 is implemented using a digital signal processing chip that forms a portion of the external programmer 142. It will, however, be appreciated that the digital filter of formula (1) can either be accomplished using a hardware solution or a software solution without departing from the spirit of the present invention.

In one application, the implantable device 100 is providing previously stored data to the external programmer 142. In another embodiment, the implantable device 100 is providing data in real time to the programmer 142. The external programmer 142 can thereby provide representations to a treating physician of both the data that is being captured by the sensor 120 and also the data that is being provided to the processor 110. As such, the treating physician can review either stored data or data being captured in real time and ascertain whether the sensor 120 or the filter 210 or the processor 110 is configured correctly for the particular condition of the patient.

From the foregoing description, it should be apparent that the implantable cardiac device system of the preferred embodiment simplifies the storage and retrieval of electrogram segments that are stored by the implantable cardiac device as a result of using a sense amplifier emulator that is a component of the external programmer 142. Hence, it is not necessary for the implantable cardiac device 100 to incorporate hardware that will allow for the selective storing of either broad band channel or sense channel electrograms, rather, only a single electrogram is stored which can subsequently downloaded and used to emulate the sense channel electrogram.

Although the foregoing description of the preferred embodiment of the present invention has shown, described and pointed out the fundamental novel features of the invention, it will be understood that various omissions, substitutions and changes in the form of the detail of the apparatus as illustrated as well as the uses thereof, may be made by those skilled in the art without departing from the spirit of the present invention. Consequently, the scope of the invention should not be limited to the foregoing discussion, but should be defined by the appended claims.

What is claimed is:

1. A system for displaying cardiac signals, comprising:
   an implantable cardiac stimulation device having:
      means for receiving a cardiac signal;
      filtering means for filtering the cardiac signal with a first filter to produce a first signal and for filtering the cardiac signal with a second filter to produce a second signal, wherein the second filter is selected to highlight a characteristic feature of heart activity;
      control means for controlling the delivery of therapeutic electrical stimulation to the heart based, at least in part, on the second signal; and
      transmitting means for transmitting the first signal; and
   an external programmer having:
      receiving means, telemetrically coupled to the transmitting means, for receiving the first signal;
      processing means for processing the first signal and generating an emulated version of the second signal; and
      displaying means for displaying at least one of the received first signal or the emulated version of the second signal.

2. The system of claim 1, wherein the first filter has a first bandwidth and the second filter has a second bandwidth that is less than the first bandwidth.

3. The system of claim 2, wherein:
   the first filter is a broad band filter and the first signal is a broad band filtered intracardiac electrogram (IEGM) signal; and
   the second filter is a narrow band filter and the second signal is a narrow band filtered intracardiac electrogram (IEGM) signal for detecting one of atrial and ventricular cardiac signals.

4. The system of claim 3, wherein the first filter has a bandwidth of between 0.1 and 400 Hz and wherein the second filter has a bandwidth of between 10 and 100 Hz.

5. The system of claim 1, wherein the external programmer can be communicatively linked to the transmitting means so as to be able to receive the first signal from the filtering means in real-time.

6. The system of claim 1, wherein the implantable cardiac stimulation device further comprises:
   a memory for storing the first signal;
   detection means for detecting when a predetermined criteria has been met; and
   wherein the control means includes means for triggering the memory to store a selected portion of the first signal when the predetermined criteria has been met.

7. The system of claim 1, wherein the displaying means is adapted to display the first signal and the emulated version of the second signal substantially simultaneously.

8. The system of claim 1, wherein the displaying means is adapted to programmably select the display of at least one of the first signal and the emulated version of the second signal.

9. The system of claim 1, wherein the emulating means comprises a digital filter that digitally filters the first signal to produce the emulated version of the second signal.

10. The system of claim 9, wherein the digital filter has an output which is a function of the current input and at least one of the previous inputs or previous outputs to the digital filter.

11. The system of claim 9, wherein the digital filter is comprised of an infinite impulse response (IIR) digital filter.

12. The system of claim 11, wherein the infinite impulse response digital filter provides an output signal as defined by the formula:

$$y(n) = \Sigma^M b_{i-0i} \cdot x(n-i) - \Sigma^N a_{j-1j} \cdot y(n-j)$$

where the coefficients $a_j$ and $b_i$ are selected so that the output $y(n)$ of the digital filter corresponds to the output of the second filter of the implantable cardiac stimulation device.

* * * * *